United States Patent
Litwiller et al.

(10) Patent No.: US 12,045,917 B2
(45) Date of Patent: Jul. 23, 2024

(54) DEEP LEARNING SYSTEMS AND METHODS OF REMOVAL OF TRUNCATION ARTIFACTS IN MAGNETIC RESONANCE IMAGES

(71) Applicant: GE PRECISION HEALTHCARE LLC, Wauwatosa, WI (US)

(72) Inventors: Daniel Vance Litwiller, Denver, CO (US); Robert Marc Lebel, Calgary (CA); Xinzeng Wang, Houston, TX (US); Arnaud Guidon, Somerville, MA (US); Ersin Bayram, Houston, TX (US)

(73) Assignee: GE Precision Healthcare LLC, Wauwatosa, WI (US)

( * ) Notice: Subject to any disclaimer, the term of this patent is extended or adjusted under 35 U.S.C. 154(b) by 260 days.

(21) Appl. No.: 17/131,171

(22) Filed: Dec. 22, 2020

(65) Prior Publication Data
US 2022/0198725 A1   Jun. 23, 2022

(51) Int. Cl.
*G06T 11/00* (2006.01)
*A61B 5/00* (2006.01)
(Continued)

(52) U.S. Cl.
CPC ............ *G06T 11/008* (2013.01); *A61B 5/055* (2013.01); *A61B 5/7203* (2013.01);
(Continued)

(58) Field of Classification Search
CPC .............. G06T 11/008; G06T 7/0012; G06T 2207/10088; G06T 2207/20081;
(Continued)

(56) References Cited

U.S. PATENT DOCUMENTS

| 7,652,474 B2 | 1/2010 | Griswold et al. |
| 10,635,943 B1 | 4/2020 | Lebel et al. |

(Continued)

FOREIGN PATENT DOCUMENTS

| CN | 207051471 U | * | 2/2018 | |
| DE | 10015068 A1 | * | 10/2001 | ........... G01R 33/561 |

OTHER PUBLICATIONS

Muckley et al., Training a Neural Network for Gibbs and Noise Removal in Diffusion MRI, May 2015, ARXIV.org. (Year: 2015).*

(Continued)

*Primary Examiner* — Wednel Cadeau

(57) ABSTRACT

A computer-implemented method of removing truncation artifacts in magnetic resonance (MR) images is provided. The method includes receiving a crude image that is based on partial k-space data from a partial k-space that is asymmetrically truncated in at least one k-space dimension. The method also includes analyzing the crude image using a neural network model trained with a pair of pristine images and corrupted images. The corrupted images are based on partial k-space data from partial k-spaces truncated in one or more partial sampling patterns. The pristine images are based on full k-space data corresponding to the partial k-space data of the corrupted images, and target output images of the neural network model are the pristine images. The method further includes deriving an improved image of the crude image based on the analysis, wherein the derived improved image includes reduced truncation artifacts and increased high spatial frequency data.

18 Claims, 14 Drawing Sheets

(51) Int. Cl.
  *A61B 5/055* (2006.01)
  *G01R 33/56* (2006.01)
  *G01R 33/565* (2006.01)
  *G06T 7/00* (2017.01)

(52) U.S. Cl.
  CPC ........ *A61B 5/7267* (2013.01); *G01R 33/5608* (2013.01); *G01R 33/565* (2013.01); *G06T 7/0012* (2013.01); *G06T 2207/10088* (2013.01); *G06T 2207/20081* (2013.01); *G06T 2207/20084* (2013.01); *G06T 2207/30004* (2013.01)

(58) Field of Classification Search
  CPC ..... A61B 5/055; A61B 5/7203; A61B 5/7267; G01R 33/5608; G01R 33/565
  See application file for complete search history.

(56) References Cited

U.S. PATENT DOCUMENTS

| | | |
|---|---|---|
| 2020/0041592 A1 | 2/2020 | Huang et al. |
| 2020/0126190 A1 | 4/2020 | Lebel |
| 2020/0202586 A1 | 6/2020 | Li et al. |

OTHER PUBLICATIONS

Xu et al., Partial Fourier Imaging in Multi-Dimensions: A Means to Save a Full Factor of Two in Time, Jan. 2001, Journal of Magnetic Resonance Imaging. (Year: 2001).*

EP application 21214630.2 filed Dec. 15, 2021—extended Search Report issued May 20, 2022; 14 pages.

Gadjimuradov Fasil et al: "Deep Recurrent Partial Fourier Reconstruction in Diffusion MRI", Oct. 21, 2020 (Oct. 21, 2020), Computer Vision—ECCV 2020 : 16th European Conference, Glasgow, UK, Aug. 23-28, 2020 : Proceedings; [Lecture Notes in Computer Science ; ISSN 0302-9743], Springer International Publishing, Cham, pp. 38-47, XP047567785, ISBN: 978-3-030-58594-5; [retrieved on Oct. 21, 2020].

Matthew J Muckley et al: "Training a Neural Network for Gibbs and Noise Removal in Diffusion MRI", arxiv.org, Cornell University Library, 201 Olin Library Cornell University Ithaca, NY 14853, May 15, 2019 (May 15, 2019), XP081793582 DOI: 10.1002/MRM. 28395 (May 15, 2019), p. 2-p. 8.

Peibei Cao et al: "Partial Fourier MRI Reconstruction Using Convolutional Neural Networks", Proceedings of the International Society for Magnetic Resonance in Medicine, 28th Annual Meeting and Exhibition, Aug. 8-14, 2020, vol. 28, 3627, Jul. 24, 2020 (Jul. 24, 2020), XP040717542, * the whole document*.

Xu Y et al: "Partial Fourier imaging in multi-dimensions: A means to save a full factor of two in time", Journal of Magnetic Resonance Imaging, Society for Magnetic Resonance Imaging, Oak Brook, IL, US, vol. 14, Jan. 1, 2001 (Jan. 1, 2001), pp. 628-635, XP002302846, ISSN: 1053-1807 * p. 1-p. 3; figure 1 *.

Muckley et al., "Learned Gibbs Removal in Partial Fourier Acquisitions for Diffusion MRI," Proc ISMRM, 2019.

Toews et al., "Deep Partial Fourier Reconstruction," Proc ISMRM, 2019, pp. 4702.

Ju et al., "Ultrafest 3D Partial Fourier Reconstruction with Well-Preserved Phase using DNN," Proc ISMRM, 2019, pp. 4708.

Pauly, "Partial k-Space Reconstruction," Stanford University, 2005, Chapter 2, pp. 11-24.

Huang et al., "Partial Fourier Reconstruction through Data Fitting and Convolution in k-Space," Magnetic Resonance in Medicine, 2009, 62: pp. 1261-1269.

Noll et al., "Homodyne Detection in Magnetic Resonance Imaging," IEEE Trans Med Imaging, 1991, 10: pp. 154-163.

Haacke et al., "A Fast Iterative, Partial-Fourier Technique Capable of Local Phase Recovery", Journal of Magnetic Resonance, 1991, 92: pp. 126-145.

Cuppen et al., "Reducing MR Imaging Time by One-Sided Reconstruction," Magnetic Resonance Imaging, 1987, 5: pp 516-527.

Antun et al., "On Instabilities of Deep Learning in Image Reconstruction and the Potential Cost of AI," PNAS 2020.

Kadimesetty et al., "Optimal Partial Fourier MRI reconstruction: Homodyne vs POCS," Proc ISMRM, 2018, pp. 3521.

Blaimer et al., "Virtual coil concept for improved parallel MRI employing conjugate symmetric signals," MRM, 2009, 61: pp. 93-102.

Ueker et al., "Robust Partial Fourier Parallel Imaging Using ESPIRIT and Virtual Conjugate Coils, " Proc ISMRM 2014, pp. 1629.

Chang et al., "High-quality and self-navigated diffusion-weighted imaging enabled by a novel interleaved block-segmented (iblocks)," Proc ISMRM, 2015, Abstract Only.

Yan et al., "Data Truncation Artificat Reduction in MR Imaging Using a Multilayer Neural Network," IEEE Transactions on Medical Imaging, 1993, vol. 12, pp. 73-77.

McGibney et al., "Quantitative Evaluation of Several Partial Fourier Reconstruction Algorithms Used in MRI," Partial Fourier Reconstruction Algorithms, University of Calgary, 1993, pp. 51-59.

Muckley et al., "Training a Neural Network for Gibbs and Noise Removal in Diffusion MRI," Magnetic Resonance in Medicine, 2020-7-14, vol. 85, 18 pages.

* cited by examiner

DEEP LEARNING SYSTEMS AND METHODS OF REMOVAL OF TRUNCATION ARTIFACTS IN MAGNETIC RESONANCE IMAGES

BACKGROUND

The field of the disclosure relates generally to systems and methods of removing truncation artifacts, and more particularly, to systems and methods of removing truncation artifacts in medical images using a neural network model.

Magnetic resonance imaging (MRI) has proven useful in diagnosis of many diseases. MRI provides detailed images of soft tissues, abnormal tissues such as tumors, and other structures, which cannot be readily imaged by other imaging modalities, such as computed tomography (CT). Further, MRI operates without exposing patients to ionizing radiation experienced in modalities such as CT and x-rays.

In MR imaging, a partial k-space is often sampled in order to increase the efficiency of the acquisition and/or to suppress artifacts. Reconstructing a partially-sampled k-space dataset results in an image that is contaminated by truncation artifacts in the form of both blurring and a characteristic ringing that severely degrades the diagnostic value of the MR image.

BRIEF DESCRIPTION

In one aspect, a computer-implemented method of removing truncation artifacts in magnetic resonance (MR) images is provided. The method includes receiving a crude image that is based on partial k-space data from a partial k-space asymmetrically truncated in at least one k-space dimension at k-space locations corresponding to high spatial frequencies. The method also includes analyzing the crude image using a neural network model. The neural network model was trained with a pair of pristine images and corrupted images. The corrupted images are based on partial k-space data from partial k-spaces truncated in one or more partial sampling patterns at the k-space locations corresponding to the high spatial frequencies, the one or more partial sampling patterns including an asymmetrical truncation in at least one k-space dimension. The pristine images are based on full k-space data corresponding to the partial k-space data of the corrupted images, and target output images of the neural network model are the pristine images. The method further includes deriving an improved image of the crude image based on the analysis, wherein the derived improved image includes reduced truncation artifacts and increased high spatial frequency data, compared to the crude image, and outputting the improved image.

In another aspect, a computer-implemented method of removing truncation artifacts in magnetic resonance (MR) images is provided. The method includes receiving a pair of pristine images and corrupted images. The corrupted images are based on partial k-space data from partial k-spaces truncated in one or more partial sampling patterns at k-space locations corresponding to high spatial frequencies, the one or more partial sampling patterns including an asymmetrical truncation in at least one k-space dimension. The pristine images are based on full k-space data corresponding to the partial k-space data of the corrupted images. The method also includes training a neural network model using the pair of the pristine images and the corrupted images by inputting the corrupted images to the neural network model, setting the pristine images as target outputs of the neural network model, analyzing the corrupted images using the neural network model, comparing outputs of the neural network model with the target outputs, and adjusting the neural network model based on the comparison. The trained neural network model is configured to reduce truncation artifacts in the corrupted images and increase high spatial frequency data in the corrupted images.

In one more aspect, a truncation artifact reduction system is provided. The system includes a truncation artifact reduction computing device, the truncation artifact reduction computing device including at least one processor in communication with at least one memory device. The at least one processor is programmed to receive a crude image that is based on partial k-space data from a partial k-space asymmetrically truncated in at least one k-space dimension at k-space locations corresponding to high spatial frequencies. The at least one processor is also programmed to analyze the crude image using a neural network model. The neural network model was trained with a pair of pristine images and corrupted images. The corrupted images are based on partial k-space data from partial k-spaces truncated in one or more partial sampling patterns at the k-space locations corresponding to the high spatial frequencies, the one or more partial sampling patterns including an asymmetrical truncation in at least one k-space dimension. The pristine images are based on full k-space data corresponding to the partial k-space data of the corrupted images, and target output images of the neural network model are the pristine images. The at least one processor is further programmed to derive an improved image of the crude image based on the analysis, wherein the derived improved image includes reduced truncation artifacts and increased high spatial frequency data, compared to the crude image, and output the improved image.

DRAWINGS

DETAILED DESCRIPTION

The disclosure includes systems and methods of removing truncation artifacts in magnetic resonance (MR) images of a subject using a deep learning model. As used herein, a subject is a human, an animal, or a phantom. Unlike signals, which represent the anatomies or structures of the subject, artifacts are visual anomalies in the medical images that are not present in the subject, which may be caused by the imaging modality such as partial sampling pulse sequences. Removing artifacts is reduction and/or removal of artifacts from an image. The systems and methods disclosed herein also synthesize missing data and interpolate high spatial frequency data, while removing truncation artifacts. Method aspects will be in part apparent and in part explicitly discussed in the following description.

In magnetic resonance imaging (MRI), a subject is placed in a magnet. When the subject is in the magnetic field generated by the magnet, magnetic moments of nuclei, such as protons, attempt to align with the magnetic field but precess about the magnetic field in a random order at the nuclei's Larmor frequency. The magnetic field of the magnet is referred to as B0 and extends in the longitudinal or z direction. In acquiring an MRI image, a magnetic field (referred to as an excitation field B1), which is in the x-y plane and near the Larmor frequency, is generated by a radio-frequency (RF) coil and may be used to rotate, or "tip," the net magnetic moment Mz of the nuclei from the z direction to the transverse or x-y plane. A signal, which is referred to as an MR signal, is emitted by the nuclei, after the excitation signal B1 is terminated. To use the MR signals to generate an image of a subject, magnetic field gradient pulses (Gx, Gy, and Gz) are used. The gradient pulses are used to scan through the k-space, the space of spatial frequencies or inverse of distances. A Fourier relationship exists between the acquired MR signals and an image of the subject, and therefore the image of the subject can be derived by reconstructing the MR signals.

Figure 1:
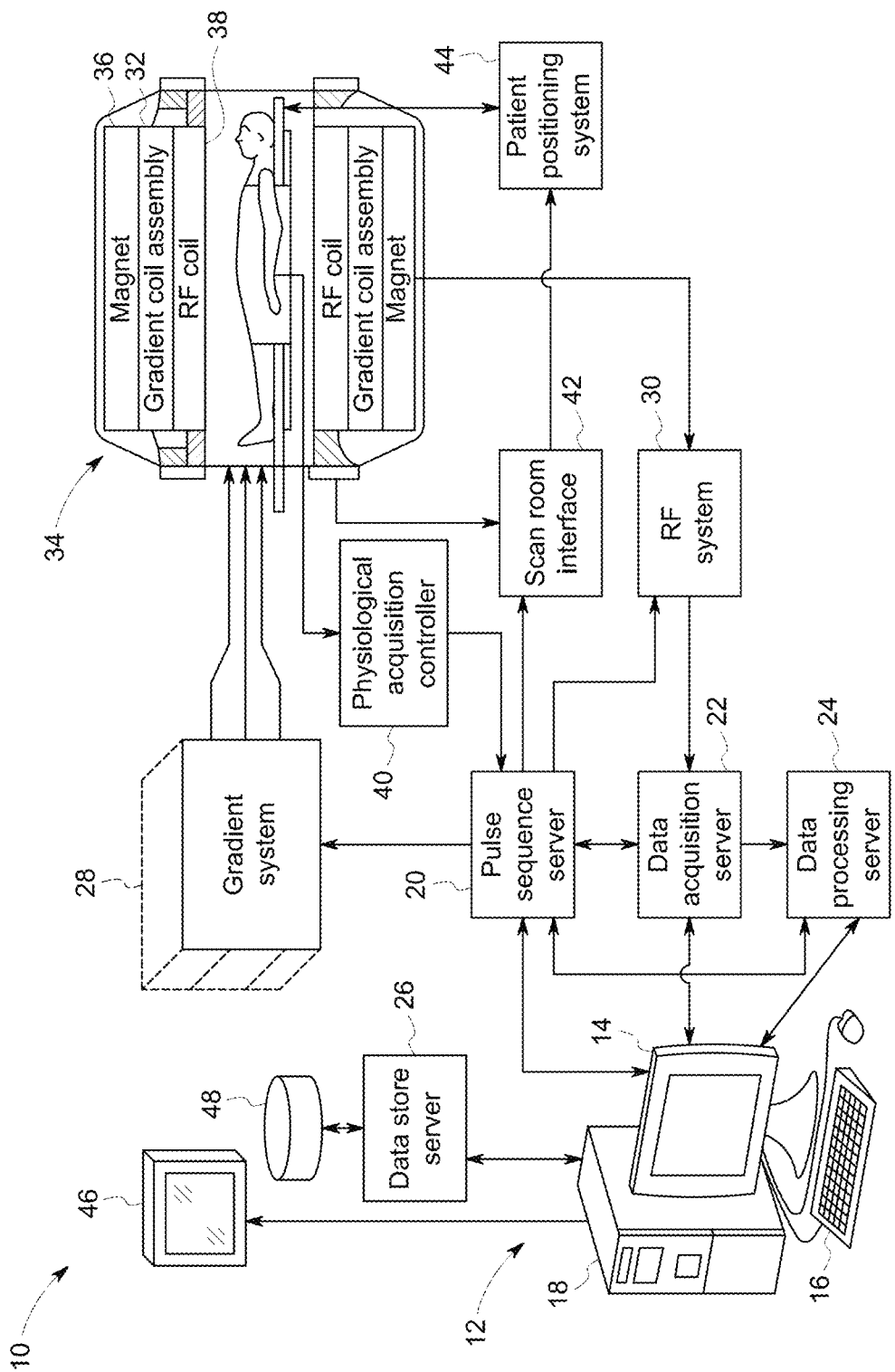
FIG. 1 is a schematic diagram of an exemplary magnetic resonance imaging (MRI) system.

FIG. 1 illustrates a schematic diagram of an exemplary MRI system 10. In the exemplary embodiment, the MRI system 10 includes a workstation 12 having a display 14 and a keyboard 16. The workstation 12 includes a processor 18, such as a commercially available programmable machine running a commercially available operating system. The workstation 12 provides an operator interface that allows scan prescriptions to be entered into the MRI system 10. The workstation 12 is coupled to a pulse sequence server 20, a data acquisition server 22, a data processing server 24, and a data store server 26. The workstation 12 and each server 20, 22, 24, and 26 communicate with each other.

In the exemplary embodiment, the pulse sequence server 20 responds to instructions downloaded from the workstation 12 to operate a gradient system 28 and a radiofrequency ("RF") system 30. The instructions are used to produce gradient and RF waveforms in MR pulse sequences. An RF coil 38 and a gradient coil assembly 32 are used to perform the prescribed MR pulse sequence. The RF coil 38 is shown as a whole body RF coil. The RF coil 38 may also be a local coil that may be placed in proximity to the anatomy to be imaged, or a coil array that includes a plurality of coils.

In the exemplary embodiment, gradient waveforms used to perform the prescribed scan are produced and applied to the gradient system 28, which excites gradient coils in the gradient coil assembly 32 to produce the magnetic field gradients $G_x$, $G_y$, and $G_z$ used for position-encoding MR signals. The gradient coil assembly 32 forms part of a magnet assembly 34 that also includes a polarizing magnet 36 and the RF coil 38.

In the exemplary embodiment, the RF system 30 includes an RF transmitter for producing RF pulses used in MR pulse sequences. The RF transmitter is responsive to the scan prescription and direction from the pulse sequence server 20 to produce RF pulses of a desired frequency, phase, and pulse amplitude waveform. The generated RF pulses may be applied to the RF coil 38 by the RF system 30. Responsive MR signals detected by the RF coil 38 are received by the RF system 30, amplified, demodulated, filtered, and digitized under direction of commands produced by the pulse sequence server 20. The RF coil 38 is described as a transmitter and receiver coil such that the RF coil 38 transmits RF pulses and detects MR signals. In one embodiment, the MRI system 10 may include a transmitter RF coil that transmits RF pulses and a separate receiver coil that detects MR signals. A transmission channel of the RF system 30 may be connected to a RF transmission coil and a receiver channel may be connected to a separate RF receiver coil. Often, the transmission channel is connected to the whole body RF coil 38 and each receiver section is connected to a separate local RF coil.

In the exemplary embodiment, the RF system 30 also includes one or more RF receiver channels. Each RF receiver channel includes an RF amplifier that amplifies the MR signal received by the RF coil 38 to which the channel is connected, and a detector that detects and digitizes the I and Q quadrature components of the received MR signal. The magnitude of the received MR signal may then be determined as the square root of the sum of the squares of the I and Q components as in Eq. (1) below:

$$M = \sqrt{I^2 + Q^2} \qquad (1);$$

and the phase of the received MR signal may also be determined as in Eq. (2) below:

$$\varphi = \tan^{-1}\left(\frac{Q}{I}\right). \qquad (2)$$

In the exemplary embodiment, the digitized MR signal samples produced by the RF system 30 are received by the data acquisition server 22. The data acquisition server 22 may operate in response to instructions downloaded from the workstation 12 to receive real-time MR data and provide buffer storage such that no data is lost by data overrun. In some scans, the data acquisition server 22 does little more than pass the acquired MR data to the data processing server 24. In scans that need information derived from acquired MR data to control further performance of the scan, however, the data acquisition server 22 is programmed to produce the needed information and convey it to the pulse sequence server 20. For example, during prescans, MR data is acquired and used to calibrate the pulse sequence performed by the pulse sequence server 20. Also, navigator signals may be acquired during a scan and used to adjust the operating parameters of the RF system 30 or the gradient system 28, or to control the view order in which k-space is sampled.

In the exemplary embodiment, the data processing server 24 receives MR data from the data acquisition server 22 and processes it in accordance with instructions downloaded from the workstation 12. Such processing may include, for example, Fourier transformation of raw k-space MR data to produce two or three-dimensional images, the application of filters to a reconstructed image, the performance of a back-projection image reconstruction of acquired MR data, the generation of functional MR images, and the calculation of motion or flow images.

In the exemplary embodiment, images reconstructed by the data processing server 24 are conveyed back to, and stored at, the workstation 12. In some embodiments, real-time images are stored in a database memory cache (not shown in FIG. 1), from which they may be output to operator display 14 or a display 46 that is located near the magnet assembly 34 for use by attending physicians. Batch mode images or selected real time images may be stored in a host database on disc storage 48 or on a cloud. When such images have been reconstructed and transferred to storage, the data processing server 24 notifies the data store server 26. The workstation 12 may be used by an operator to archive the images, produce films, or send the images via a network to other facilities.

MR signals are represented by complex numbers, where each location at the k-space is represented by a complex number, with I and Q quadrature MR signals being the real and imaginary components. Complex MR images may be reconstructed based on I and Q quadrature MR signals, using processes such as Fourier transform. Complex MR images are MR images with each pixel represented by a complex number, which also has a real component and an imaginary component.

In MRI, asymmetric sampling in the frequency and phase encoding directions or dimensions is referred to as fractional echo and partial number of acquisition (NEX), respectively, and is widely used in both 2D and 3D MR imaging. These undersampling techniques are typically used to shorten echo times (e.g. to increase SNR or alter tissue contrast), to shorten repetition times (e.g. to reduce scan time), and/or to suppress unwanted artifacts (such as fineline artifact in fast-spin echo (FSE) imaging or off-resonance artifacts in gradient recalled echo (GRE) and echo planar imaging (EPI)). Asymmetric sampling of k-space introduces truncation artifacts into the reconstructed images, both in the form of blurring and ringing. Various image reconstruction techniques have been devised, therefore, for reconstructing partial k-space data, such as conjugate synthesis, homodyne, and projection onto convex sets (POCS). These known techniques rely on some intrinsic estimate of the underlying image phase, which can be subsequently removed (or "corrected"), allowing the synthesis of the missing or unsampled data based on the principle of Hermitian symmetry of real-valued signals. This phase estimate is often derived from the central, symmetrically-sampled portion of k-space, and is limited in several important ways. First, the phase estimate is contaminated by thermal noise, which is especially problematic in low-signal image regions and/or when this phase estimate performed on a per-channel (or per-view) basis. Secondly, this phase estimate is inherently band-limited, and must be further low-pass filtered upon application to prevent the introduction of additional truncation artifacts. Therefore, high spatial frequency phase information is not corrected, leaving residual blurring in the final reconstructed image. The application of this low-frequency phase estimate also tends to bias the noise in the reconstructed image, which would otherwise tend to be normally distributed. The appearance of this biased noise signal in the reconstructed image degrades the image contrast, especially in low-signal regions, and the altered distribution of this noise degrades noise-averaging performance (as in multi-NEX EPI-diffusion) and/or complicate downstream denoising efforts, which are generally based on an assumed noise model. Further, the known partial k-space reconstruction techniques tend to exhibit various strengths and weaknesses, and the choice of method tends to result in various performance tradeoffs. POCS, for example, tends to localize reconstruction artifacts, whereas homodyne tends to result in contrast errors. Finally, in the case of homodyne and conjugate synthesis, the phase information is discarded during reconstruction, making them unsuitable for phase-sensitive applications, such as Dixon chemical shift imaging, phase-sensitive inversion recovery imaging, and generation of phase-sensitive maps based on the phases of the images.

Using deep learning to directly remove these asymmetric truncation artifacts provides superior performance to conventional methods. The deep learning approach involves no explicit phase correction, no low-pass filtering, and no conventional filtering of any kind. Unlike the conventional methods mentioned above, the deep learning approach makes use of all acquired data (versus a low-pass filtered phase estimate) and this results in a reconstructed image with sharper edges, truer contrast, and less noise bias. Moreover, the underlying phase of the image after truncation artifact removal is well-preserved, even at high frequencies, making this technique suitable for phase sensitive imaging applications. In addition to reduce truncation artifacts, the systems and methods described herein also increase or recover the missing high spatial frequency data caused by asymmetrical and/or symmetrical truncation.

Figure 2A:
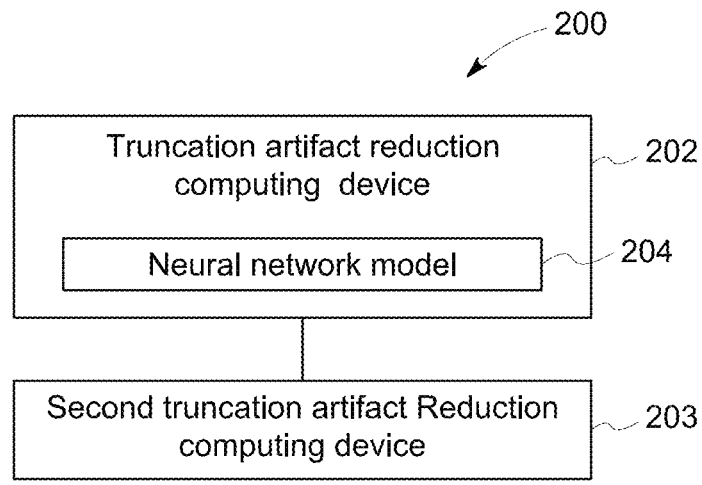
FIG. 2A is an exemplary truncation artifact reduction system.

FIG. 2A is a schematic diagram of an exemplary truncation artifact reduction system 200. In the exemplary embodiment, the system 200 includes a truncation artifact reduction computing device 202 configured to reduce truncation artifacts and increase high spatial frequency data. The computing device 202 further includes a neural network model 204. The system 200 may include a second truncation artifact reduction computing device 203. The second truncation artifact reduction computing device 203 may be used to train the neural network model 204, and the truncation artifact reduction computing device 202 may then use the trained neural network model 204. The second truncation artifact reduction computing device 203 may be the same computing device as the truncation artifact reduction computing device 202 such that the training and use of the neural network model 204 are on one computing device. Alternatively, the second truncation artifact reduction computing device 203 may be a computing device separate from the truncation artifact reduction computing device 202 such that the training and use of the neural network model 204 are executed on separate computing devices. The truncation artifact reduction computing device 202 may be included in the workstation 12 of the MRI system 10, or may be included on a separate computing device that is in communication with the workstation 12.

Figure 2B:
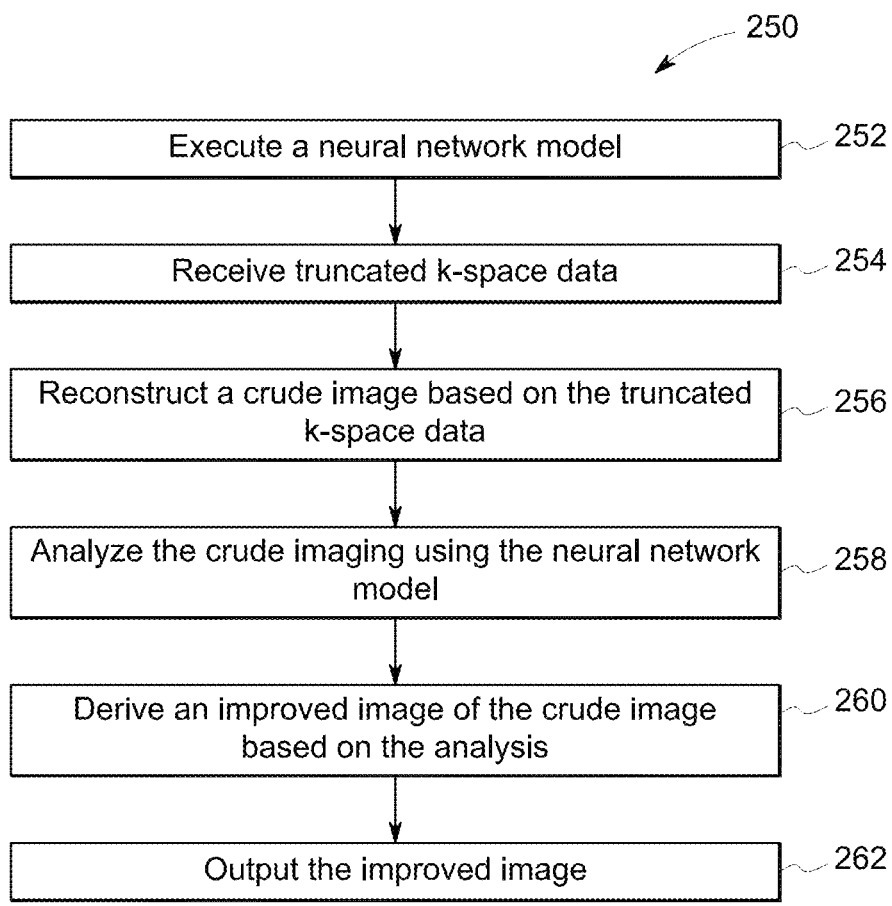
FIG. 2B is a flow chart of an exemplary method of reducing truncation artifacts.

FIG. 2B is a flow chart of an exemplary method 250. The method 250 may be implemented on the truncation artifact reduction system 200. In the exemplary embodiment, the method includes executing 252 a neural network model for analyzing MR images. The neural network model is trained with training images. The training images may be pairs of pristine images and corrupted images, and the target output images of the neural network model are the pristine images. The corrupted images are images reconstructed based on partial k-space data from a partial k-space in one or more partial sampling patterns of the k-space. As used herein, partial sampling or truncation is partial sampling of the k-space in one or more dimensions of the k-space by truncating the k-space in those dimensions at locations corresponding to high spatial frequencies. High spatial frequencies are located at the peripheral of the k-space, compared to low-spatial frequencies, which are located at and around the center of the k-space. The truncation of the k-space causes truncation artifacts such as blurring and ringing in the corrupted images. The pristine images are images based on a full k-space corresponding to the partial k-space.

Figure 2C:
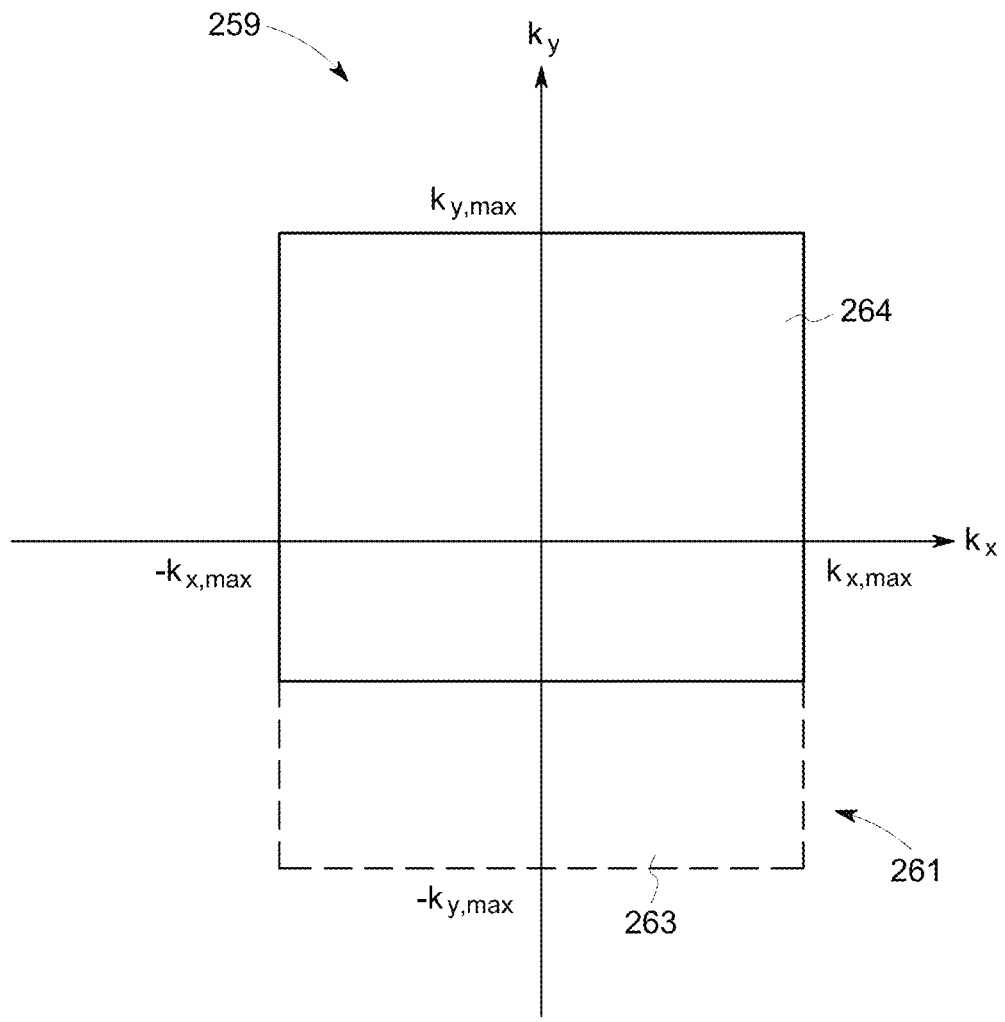
FIG. 2C is a schematic diagram of a partial k-space sampling.

FIG. 2C is a schematic diagram of a partial sampling pattern or truncation pattern 259 of a full k-space 261. A full k-space 261 is defined by the maximum kx or ky values $k_{x,max}$ and $k_{y,max}$, which is defined by maximum frequency- or phase-encoding gradients. In partial sampling, part of the high spatial frequency data 263 is not acquired. Truncation may be in the kx dimension and/or the ky dimension, and may be in the kz dimension in a three-dimension (3D) acquisition. The full k-space 261 is truncated into a partial k-space 264. The partial k-space 264 shown in FIG. 2A is the full k-space 261 truncated in the ky dimension, where negative high spatial frequency data are not acquired during the image acquisition of the partial k-space 264. Truncation may be asymmetrical, where the k-space is truncated asymmetrically in a dimension. The partial k-space 264 shown in FIG. 2A is asymmetrical truncated in the ky dimension. The truncation may be symmetrical, where the k-space is truncated symmetrically at k-space locations of positive and negative spatial frequencies. Truncation may be symmetrical and asymmetrical in one dimension, where k-space is truncated at k-space locations for both positive and negative spatial frequencies but in an unequal amount. Truncation reduces high-spatial frequency data and causes truncation artifacts. Truncation along the axes of a 2D Cartesian coordinate system as shown in FIG. 2C is illustrated as an example only. The systems and methods described herein may also be used for removal of truncation artifacts in images based on k-space data from a k-space that is asymmetrically truncated along the axes of a 2D/3D Cartesian coordinate system, a 2D/3D non-Cartesian coordinate system such as a polar, spherical, or cylindrical coordinate system, or a combination thereof. For example, the partial sampling pattern is the k-space being asymmetrically truncated in a radial dimension. In another example, the k-space data are acquired as a stack of radial lines in the kx-ky planes along the kz direction and a partial sampling pattern is the k-space being asymmetrically truncated in a radial dimension in the kx-ky plane and asymmetrically truncated in the kz dimension.

In the exemplary embodiment, the corrupted images for training may be in various partial sampling patterns in various partial sampling factors or partial k-space factor. A partial k-space factor is the ratio between the partial k-space in the truncation dimension and the full k-space. For example, if the partial k-space factor is 0.5 in the ky dimension, only half of the k-space, the positive ky half or the negative ky half, is acquired. In some embodiments, the corrupted images and the pristine images are simulated image. The neural network model 204 may be trained with one partial sampling pattern and configured to remove truncation artifacts and increase high spatial frequency data for corrupted images based on MR k-space data from a partial k-space acquired in that partial sampling pattern. For example, the neural network model 204 is trained with pairs of corrupted images and pristine images for asymmetrical truncation in the kx dimension, the trained neural network model 204 is specialized in removing truncation artifacts and increase high spatial frequency data in the kx dimension for images acquired with asymmetrical truncation in the kx dimension. On the other hand, the neural network model 204 may be a general neural network model 204 that is configured to remove truncation artifacts and increase high spatial frequency data for partial k-space data acquired in various partial sampling patterns. A general neural network model 204 may be trained by pairs of corrupted images and pristine images for various partial sampling patterns. A specialized neural network model 204 takes less time and computation burden to train than a general neural network model 204.

In some embodiments, the neural network model 204 includes one or more layers of neurons configured to reconstruct an image based on partial k-space data. During training, partial k-space data in various partial sampling patterns are used for training, where the partial k-space data are the inputs to the neural network model 204.

Referring back to FIG. 2B, the method 250 further includes receiving 254 partial k-space data from a partial k-space that is truncated in at least one dimension. The method 250 also includes reconstructing 256 a crude image based on the partial k-space data. The crude image may be reconstructed by zero-filling the partial k-space data with zeros at locations corresponding to the skipped k-space locations to derive full k-space data, and then reconstructing the crude image based on the zero-filled k-space data. The full k-space data for the crude image may be reconstructed by methods other than zero-filling, such as interpolation. Reconstructing 256 the crude image may be carried out outside the neural network model 204 and the crude image is inputted into the neural network model. Alternatively, reconstructing 256 the crude image is conducted by the neural network model 204, where partial k-space data are directly input into the neural network model 204, and the neural network model 204 includes one or more layers of neurons configured to reconstruct a crude image based on the partial k-space data. Further, the method 250 includes analyzing 258 the crude image. In addition, the method 250 includes deriving 260 an improved image of the crude image based on the analysis. The neural network model 204 outputs an improved image, an image of improved image quality, corresponding to the crude image. The improved image has reduced truncation artifacts and increased high spatial-frequency data, compared to the crude image. In some embodiments, the neural network model 204 includes one or more layers of neurons configured to generate full k-space data by methods such as Fourier transforming the improved image inferenced by the neural network model 204. The method 250 also includes outputting 262 the improved images.

Figure 3A:
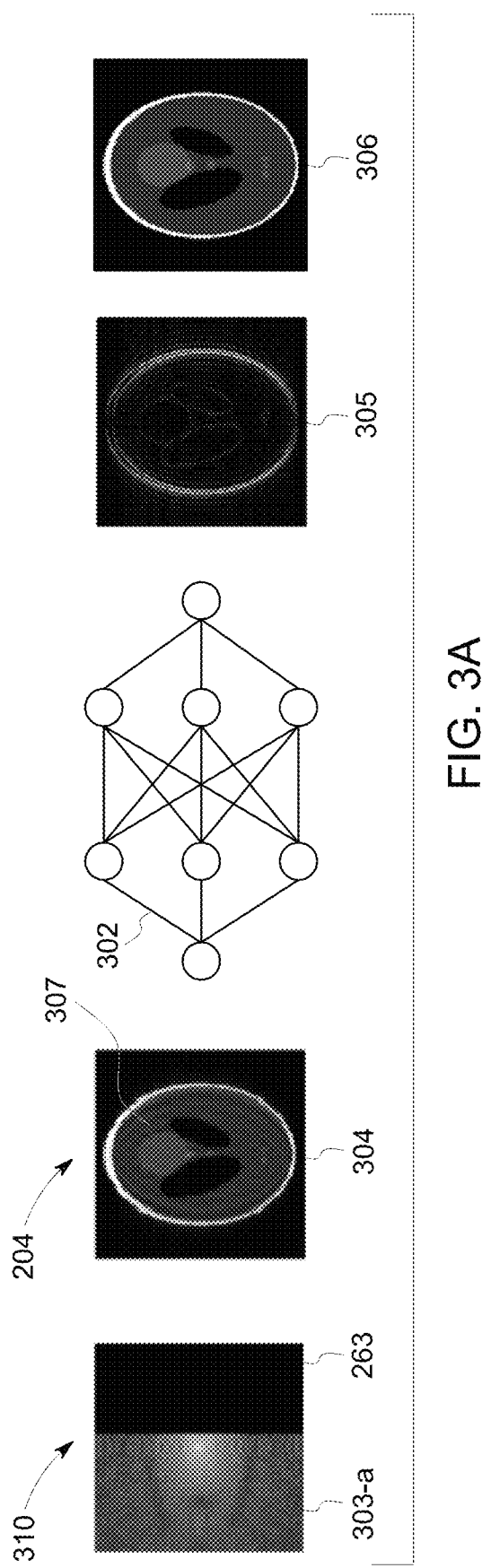
FIG. 3A is an exemplary neural network model for the system shown in FIG. 2A.
Figure 3B:
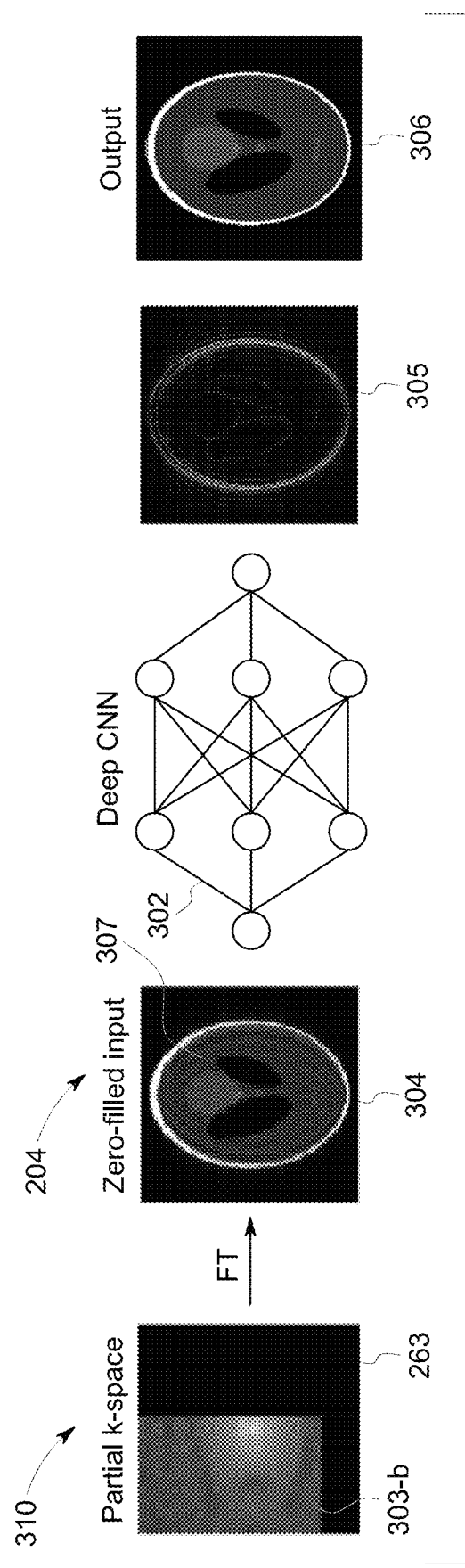
FIG. 3B is another exemplary neural network model for the system shown in FIG. 2A.
Figure 3C:
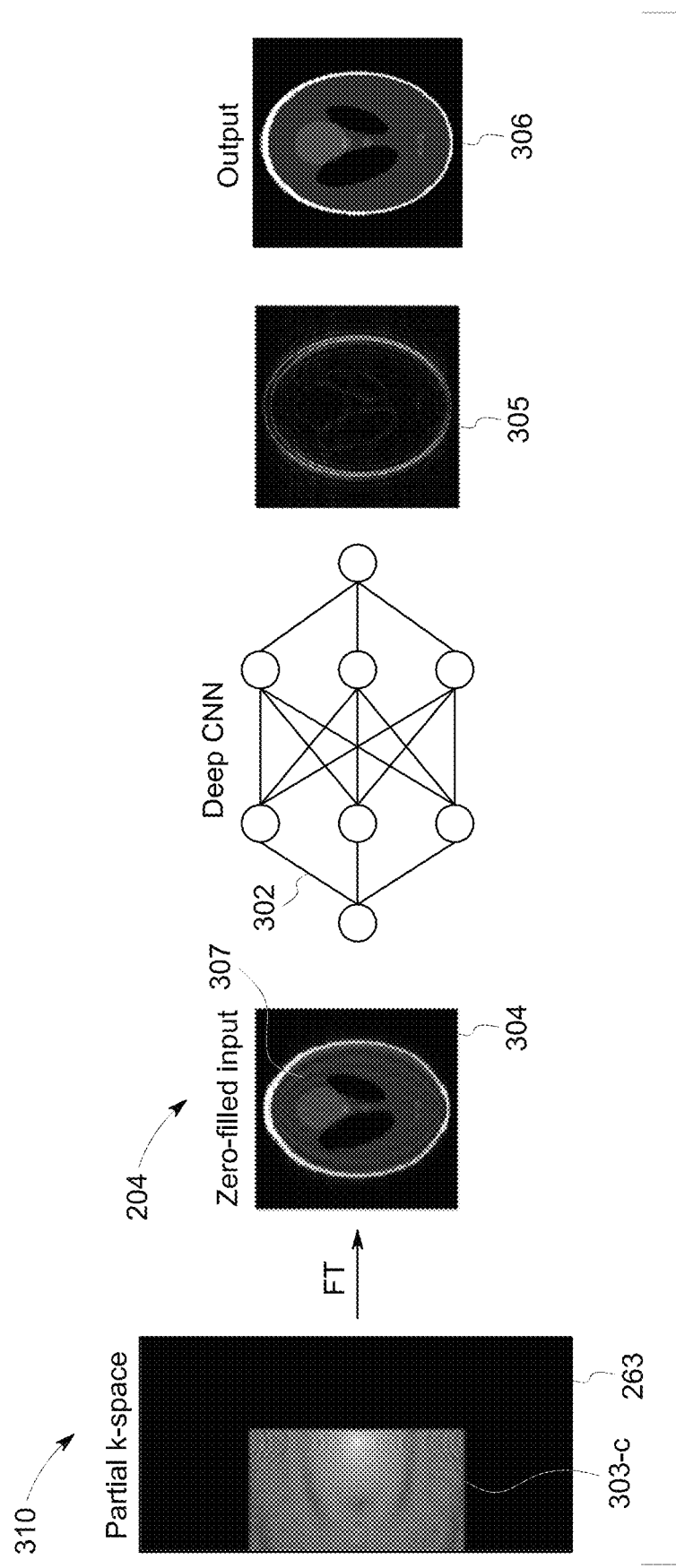
FIG. 3C is one more exemplary neural network model for the system shown in FIG. 2A.
Figure 3D:
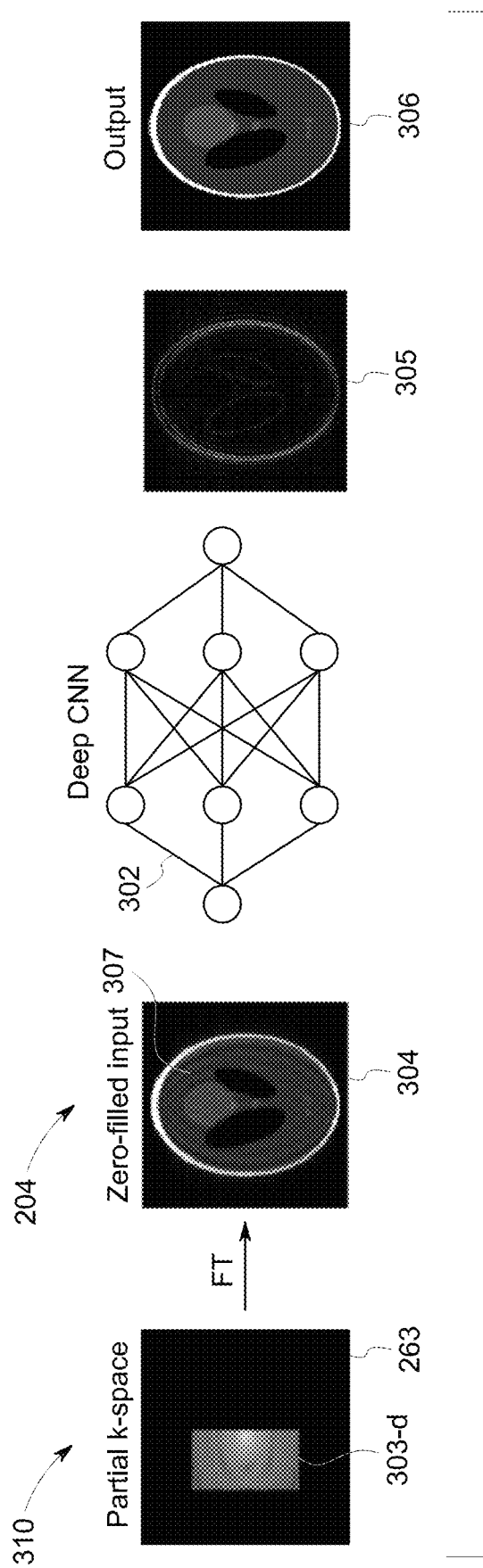
FIG. 3D is yet one more exemplary neural network model for the system shown in FIG. 2A.

FIGS. 3A-3D are schematic diagrams of exemplary neural network model 204. The neural network model 204 may include a convolutional neural network 302. The neural network 302 is trained with corrupted images 304 as inputs and output pristine images 306. Compared to the corrupted images 304, artifacts 307 such as truncation artifacts are reduced and missing high spatial frequency data 263 are recovered in the pristine images 306. In the exemplary embodiment, partial k-space data 303 missing high spatial frequency data 263 is received. The differences among FIGS. 3A-3D are the different partial sampling patterns in acquiring partial k-space data 303-a, 303-b, 303-c, 303-d (collectively referred to as partial k-space data 303). In FIG. 3A, for the partial k-space data 303-a, the k-space 310 is truncated asymmetrically in one dimension, such as the kx dimension, where the positive kx portion of the k-space 310 is skipped while the negative kx portion is fully acquired. In FIG. 3B, for the partial k-space data 303-b, the k-space 310 is truncated asymmetrically in two dimensions, such as the kx and the ky dimensions. In FIG. 3C, for the partial k-space data 303-c, the k-space 310 is truncated asymmetrically in the kx dimension and symmetrically in the ky dimension. In FIG. 3D, for the partial k-space data 303-d, the k-space 310 is truncated asymmetrically in the kx dimension and additionally symmetrically truncated in both the kx and ky dimensions. That is, the partial k-space data 303 has a varying partial sampling pattern. In the various partial sampling patterns, the partial sampling factor in the kx or ky dimension may vary. The neural network model is configured to reduce truncation artifacts and recover the missing k-space data for the partial k-space data in varying partial sampling patterns.

In some embodiments, the neural network 302 is trained with the corrupted images 304 as inputs and residual images 305 as target outputs. The residual images 305 are difference images between the corrupted images 304 and ground truth images 306, which are based on full k-space data corresponding to the partial k-space data 303-a, 303-b, 303-c, 303-d. In FIGS. 3A and 3B, the residual image 305 is an image of asymmetrical truncation artifacts of the corrupted image 304. In FIGS. 3C and 3D, the residual image 305 is an image of asymmetrical truncation artifacts and symmetrical truncation artifacts of the corrupted image 304 and of high spatial frequency data at spatial frequencies higher than those of the partial k-space data 303-c, 303-d.

The output of the neural network 302 may be a residual image or an improved image of the input to the neural network model 204. When the output of the neural network 302 is a residual image, the neural network model 204 may include one or more layers of neurons configured to generate an improved image based on the output residual image. For example, the improved image is computed as the input image being subtracted by the residual image. As a result, the output image has reduced truncation artifacts and increased high spatial frequency data, compared to the input image to the neural network model 204. Alternatively, the neural network model 204 outputs a residual image, and the generation of an improved image based on the residual image is carried out outside the neural network model. In one embodiment, a user is provided with options, such as outputting an improved image, a residual image, or both.

The neural network model 204 may be specialized such as being trained to reduce truncation artifacts and recover missing k-space data from asymmetrical truncation in one dimension. The neural network model 204 may be generalized such as being trained to reduce truncation artifacts and recover missing k-space data from asymmetrical truncation in one or more dimensions and/or symmetrical truncation in one or more dimensions. As more generalized the neural network model 204 gets, more training data is needed for training the neural network model 204 for the neural network model to be used to inference of improved images for partial k-space data in various truncation patterns and truncation factors. The computation burden therefore is increased. For example, to train the neural network model shown in FIG. 3A, asymmetrical partial k-space data in the same dimension of various partial sampling factors or corrupted images based on such partial k-space data are provided as inputs. In another example, to train the neural network model shown in FIG. 3D, corrupted images based on partial k-space data in various symmetrical partial sampling factors in the kx dimension, various symmetrical partial sampling factors in the ky dimension, and various asymmetrical partial sampling factors in the kx dimension are provided as inputs. Because the number of training image pairs are largely increased and complexity of partial sampling patterns is greatly increase, the complexity of the truncation artifacts increases and the training of the neural network model 204 in FIG. 3D is much more computationally intensive and time consuming that that of the neural network model 204 in FIG. 3A.

Figure 4A:
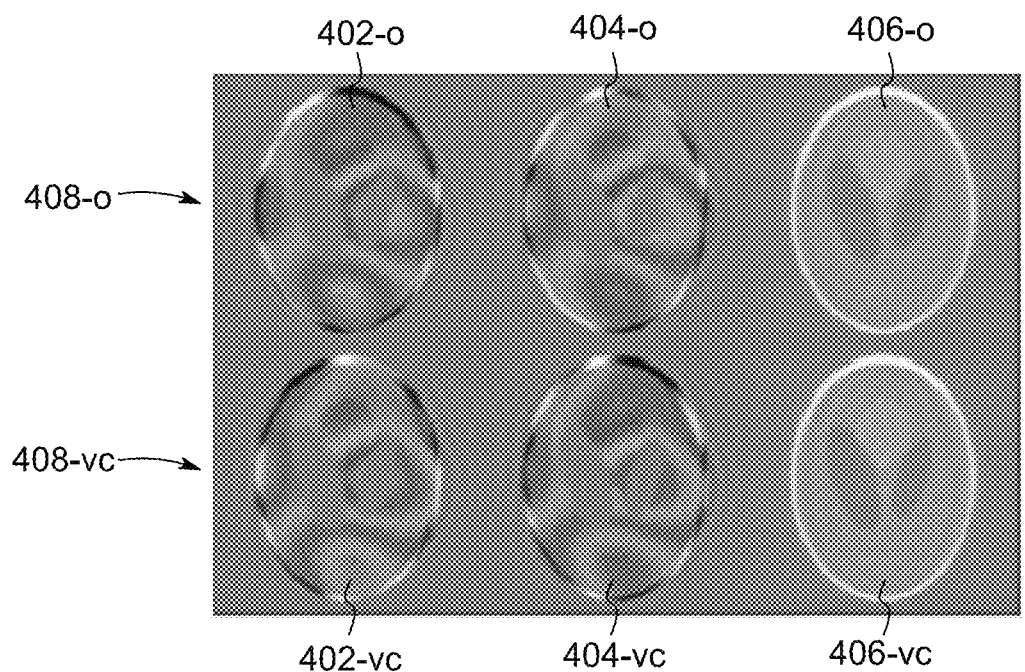
FIG. 4A is a comparison of a complex image and the corresponding conjugate reflection image.
Figure 4B:
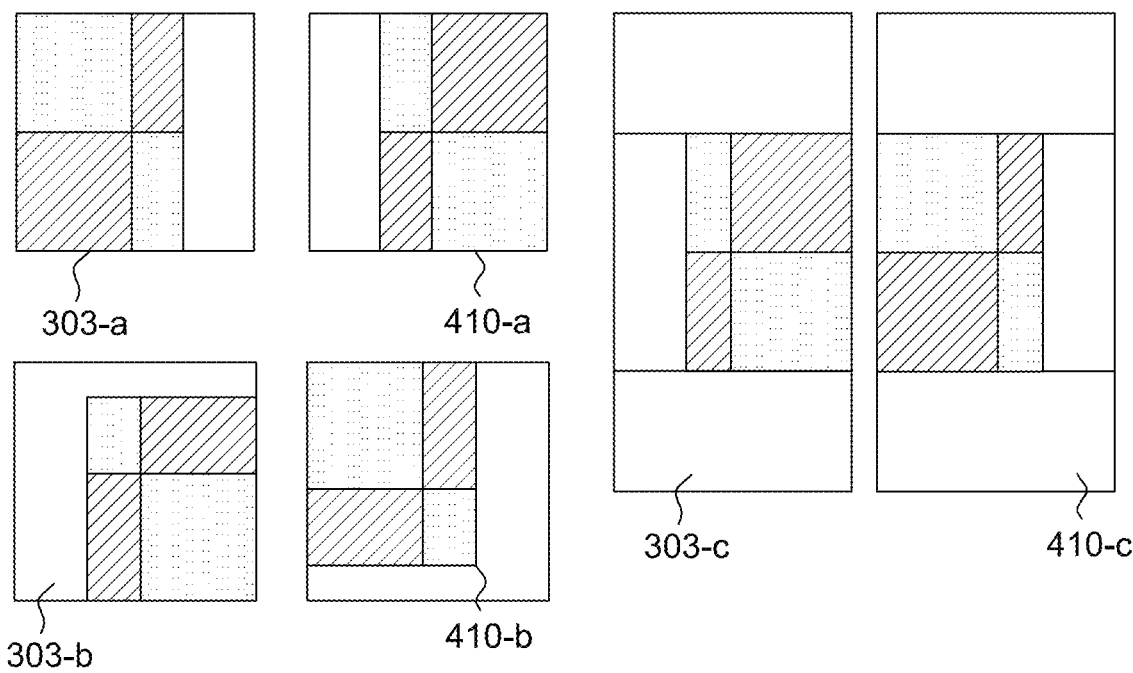
FIG. 4B shows schematic diagrams of conjugate reflections.
Figure 4C:
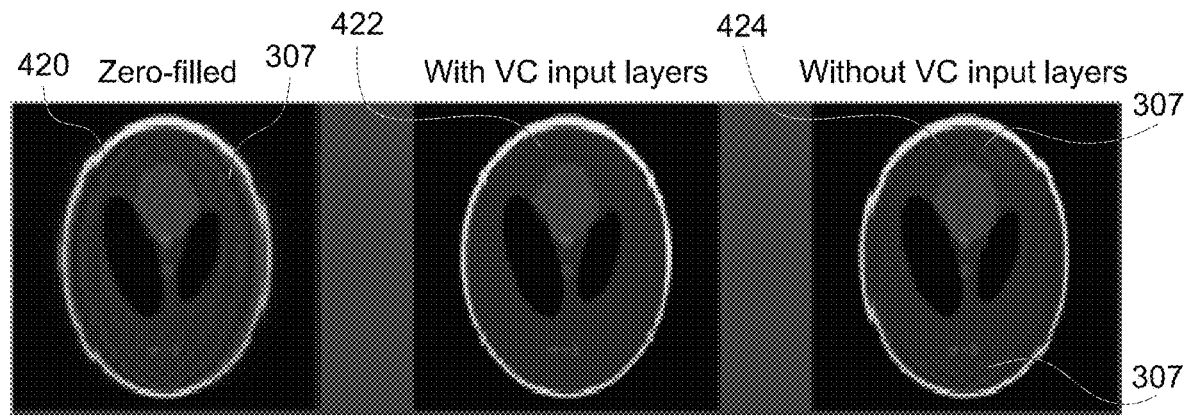
FIG. 4C is a comparison of a zero-filled reconstructed image and images output from the neural network model shown in FIG. 2A with and without inputs of conjugate reflections.

In one embodiment, the neural network model 204 includes input layers for conjugate reflections of k-space data or conjugate reflection images reconstructed from the conjugate reflections (FIGS. 4A-4C). As described above, MRI signals/k-space data and an MR image are represented by complex numbers. A conjugate reflection of k-space data at k-space location k is a complex conjugate of the k-space data at k-space location−k, as shown in Eq. (3) below:

$$S_{cf}(k)=S^*(-k), \quad (3)$$

where $S_{cf}(k)$ is a conjugate reflection at k-space location k, S(−k) is the original k-space data at k-space location−k, and * represents a complex conjugate.

In other words, to synthesize a conjugate reflection of the original k-space data, each complex number at each k-space location is conjugated and reflected across the origin. For example, k-space data in the first quadrant in the conjugate reflection are complex conjugates of the original k-space data in the third quadrant. A conjugate reflection image is derived by Fourier transform of the conjugate reflections. Conjugate reflections or conjugate reflection images may be input into the neural network model 204 during the training as part of the training corrupted images, or during inferencing as being inputted together with the original partial k-space data or crude images based on the original partial k-space data. FIG. 4A shows a comparison of a real component 402-o, 402-vc, an imaginary component 404-o, 404-c, and a magnitude component 406-o, 406-vc of an original complex image 408-o and the conjugate reflection image 408-vc of the complex image 408-o. The magnitude images 406-o, 406-vc are the same. FIG. 4B shows exemplary conjugate reflections 410-a, 410-b, 410-c of original k-space data 303-a, 303-b, 303-c. The original k-space data 303-a, 303-b, 303-c were acquired with different k-space partial sampling patterns (also see FIGS. 3A-3C), where the k-space is asymmetrically truncated in the kx-dimension in k-space data 303-a, asymmetrically truncated in both the kx- and ky dimensions in the k-space data 303-b, and asymmetrical truncated in the kx-dimension and symmetrically truncated in the ky dimension in the original k-space data 303-c.

FIG. 4C shows a comparison of an image 420 reconstructed with zero-filling, an image 422 output by the neural network model 204 having conjugate reflection input layers, and an image 424 output by the neural network model 204 without conjugate reflection input layers. The partial k-space data is from a partial k-space asymmetrically truncated in the left-right (kx) dimension and symmetrically truncated in both the kx and ky dimensions with a zero filling interpolation (ZIP) factor of 2. A ZIP factor indicates the extent of symmetrical zero padding in the kx or ky dimension. The image resolution of the reconstructed image with zero padding is increased by a factor indicated by the ZIP factor. For example, if the image resolution before the zero padding is 128×128, the reconstructed image by zero padding with a ZIP factor of 2 in both dimensions has an image resolution of 256×256. In the neural network model with conjugate reflection input layers, conjugate reflections of the partial k-space data are provided as additional inputs to the neural network model 204. The image 422, 424 output by the neural network model 204 with or without additional inputs of conjugate reflections has reduced truncation artifacts 307, compared to the image 420 reconstructed by zero-filling. Compared to the image 424, the artifacts 307 in the image 422 output by the neural network model 204 with additional inputs of conjugate reflections is further reduced to a level of being not visually noticeable. Conjugate reflections 410 provide a different representation of the partial k-space data 303, and improve the image quality output from the neural network model 204.

Figure 5:
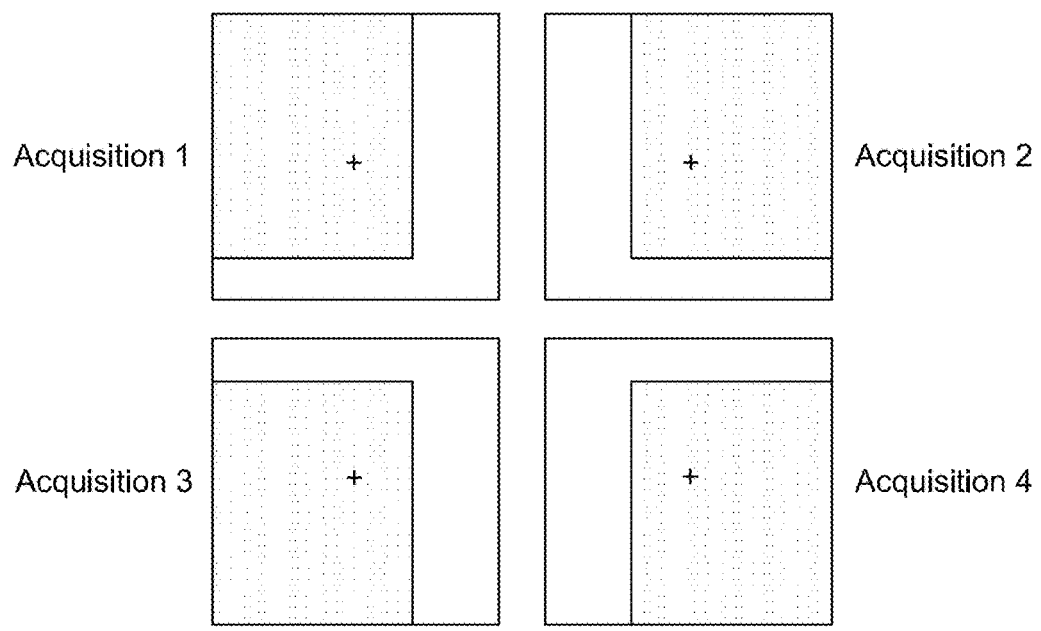
FIG. 5 is a schematic diagram of a multi-acquisition pulse sequence.

FIG. 5 shows an embodiment of acquiring k-space data of various partial sampling patterns in a multi-acquisition pulse sequence. In the exemplary embodiment, four acquisitions are acquired. The multiple acquisitions may be acquired as multiple shots, multiple phases, or multiple number of acquisitions (NEX). The k-space is asymmetrically truncated in the kx and the ky dimensions. In acquisition 1, positive kx and negative ky locations are truncated, where k-space data at those locations are not acquired. In acquisition 2, negative kx and negative ky locations are truncated. In acquisition 3, positive kx and positive ky locations are truncated. In acquisition 4, negative kx and positive ky locations are truncated. To adjust the partial sampling pattern in the kx-dimension, the echo time may be adjusted to sample different portion of the echo. To adjust the partial sampling pattern in the ky-dimension, in Cartesian acquisition, ky lines of the truncated locations are not acquired, where truncated locations are locations in the k-space that k-space data are not acquired. The partial k-space data from the multiple acquisitions are input into the neural network model 204. The k-space data from the multiple acquisitions are acquired with complementary partial sampling patterns, where k-space locations not sampled in one acquisition are sampled in at least one of the other acquisitions, and provide complementary information in the k-space data to each other. The complementary sampling patterns along axes of a 2D Cartesian coordinate system described above are illustrated as an example only. Similar to truncation patterns, complementary sampling patterns may be along axes of a 2D/3D Cartesian coordinate system, a 2D/3D non-Cartesian coordinate system such as a polar, spherical, or cylindrical coordinate system, or a combination thereof. The k-space data from the multiple acquisitions are jointly processed by the neural network model 204, and in the meantime, the image quality of the image from each acquisition and a composite image from a combination of the multiple acquisitions is improved due to the complementary information.

Figure 6:
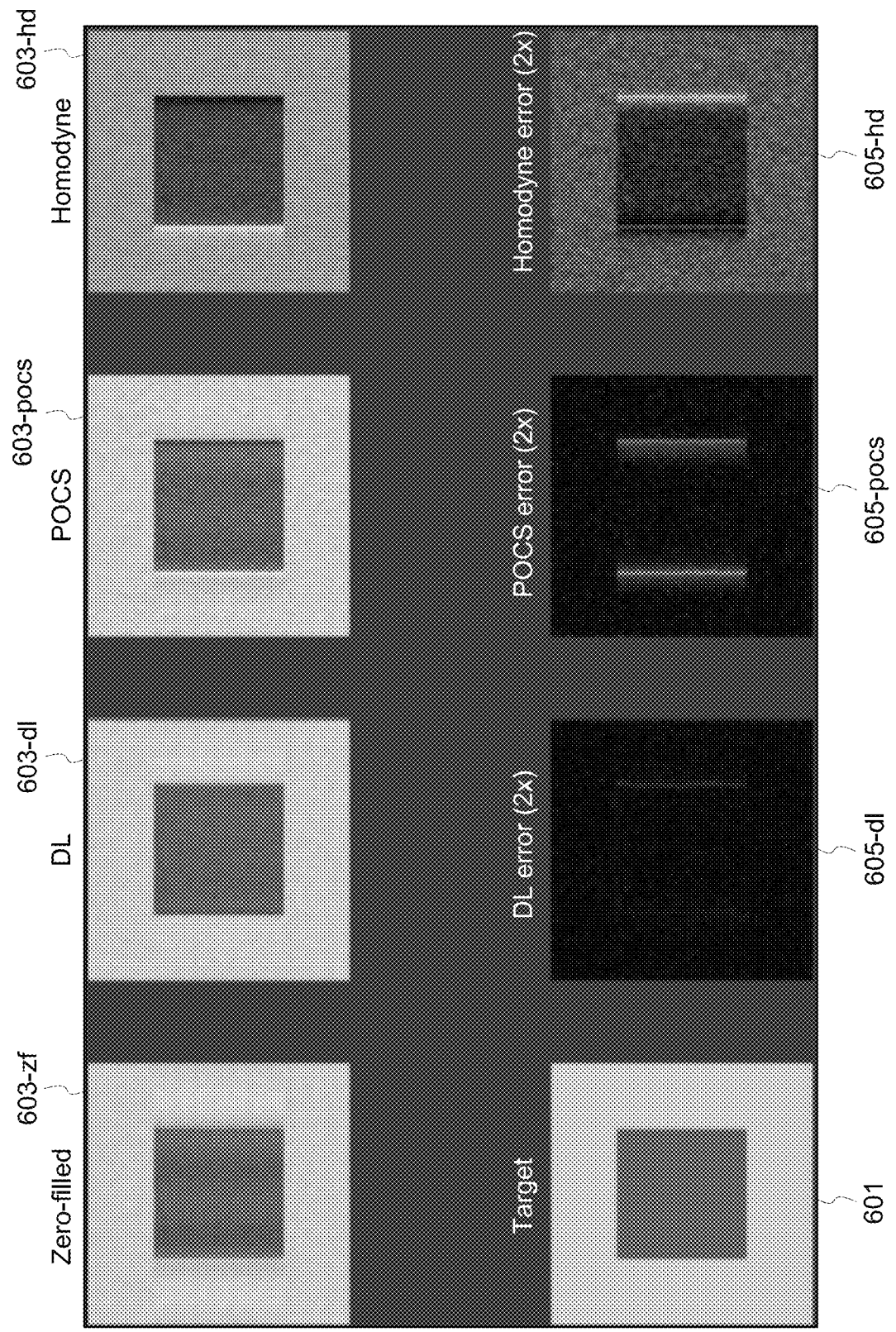
FIG. 6 is a comparison of digital phantom images reconstructed with known methods and using the neural network model shown in FIG. 2A.

FIG. 6 is a comparison of images of a digital phantom reconstructed with the deep learning (DL) methods described herein and with known methods. An image 601 is the target image. Images 603-zf, 603-dl, 603-pocs, 603-hd are images reconstructed by zero-filing, the methods described herein, POCS, and homodyne, respectively. Images 605-dl, 605-pocs, 605-hd are the differences between the target image 601 and the reconstructed images 603-zf, 603-dl, 603-pocs, 603-hd. In this example, the neural network model 204 was trained to remove truncation artifacts in the left-right (kx) dimension only. The partial sampling factor was 0.54. As shown in FIG. 6, the systems and methods described herein outperform both iterative POCS and homodyne reconstruction methods in terms of edge sharpness and contrast preservation.

Figure 7:
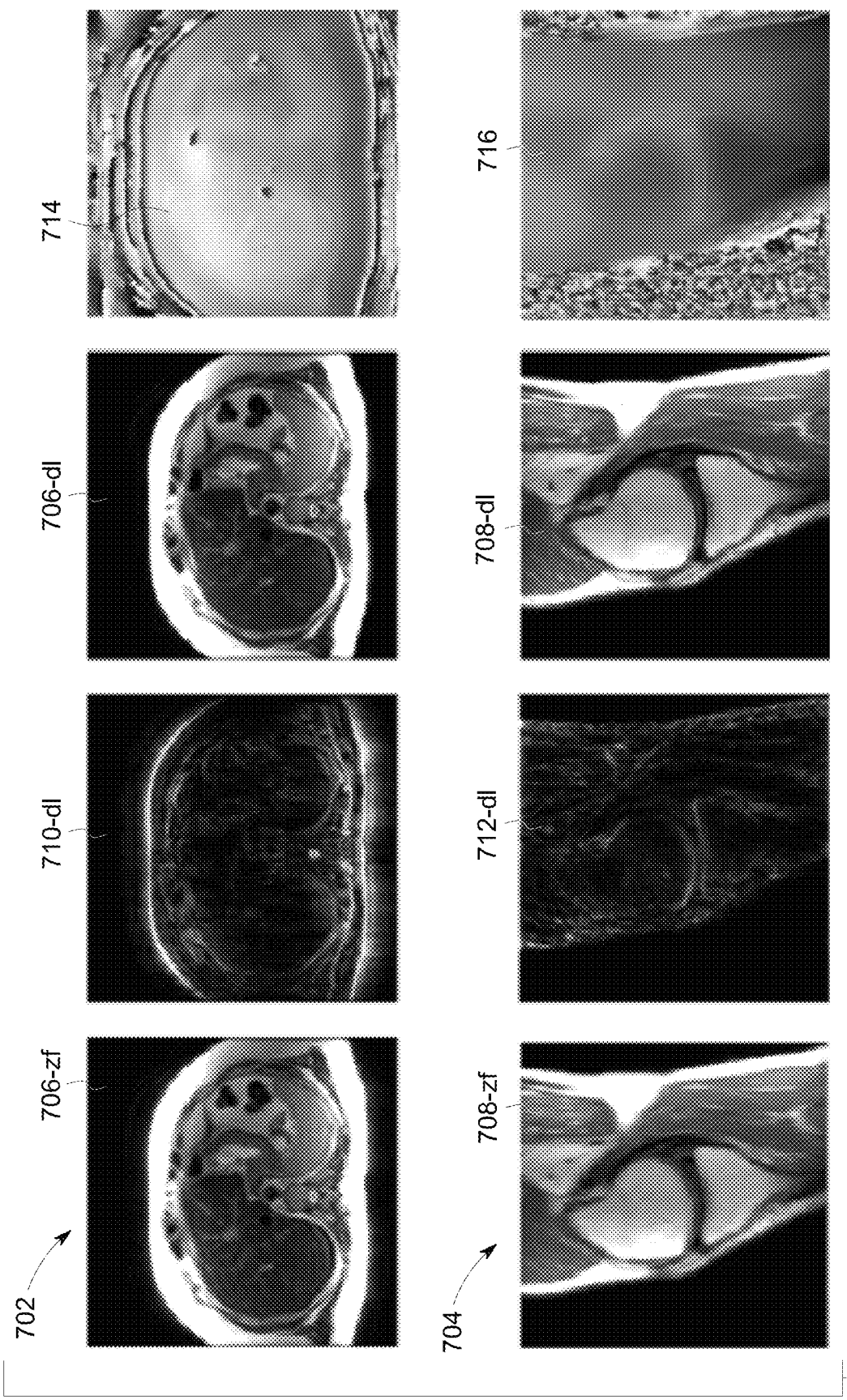
FIG. 7 is a comparison of human images reconstructed by zero-filling and using the neural network model shown in FIG. 2A.

FIG. 7 shows axial abdominal images 702 (top row) and sagittal knee images 704 (bottom row) images reconstructed with zero-filling and the DL methods described herein. The Abdominal images 702 are acquired with a single-shot fast spin-echo sequence. The knee images 704 are acquired with a fast spin-echo sequence. Images 706-zf, 708-zf are magnitude images reconstructed by zero-filling. Images 710-dl, 712-dl are residual images output by the neural network model 204 that include truncation artifacts. Images 706-dl, 708-dl are magnitude images of images reconstructed by DL methods. Images 714, 716 are phase images of images reconstructed by DL methods. As shown in FIG. 7, the truncation artifacts in images 706-dl, 708-dl are largely reduced when reconstructed by DL methods, compared to images 706-zf, 708-zf when reconstructed by zero-filling. Phase information is substantially preserved, as shown in images 714, 716. In this example, the neural network model 204 is trained for half NEX and ZIP factor 2 in both phase- and frequency-encoding dimensions.

In some embodiments, k-space data is acquired by a multi-channel/multi-coil RF coil, and the input to the neural network model 204 is k-space data or an image acquired by individual channels of the RF coil. The k-space data or images acquired by individual coils are input into the neural network model 204 separately and the outputs from the neural network model 204 are combined into one image. Coil sensitivity maps are applied in generating the combined image.

Figure 8A:
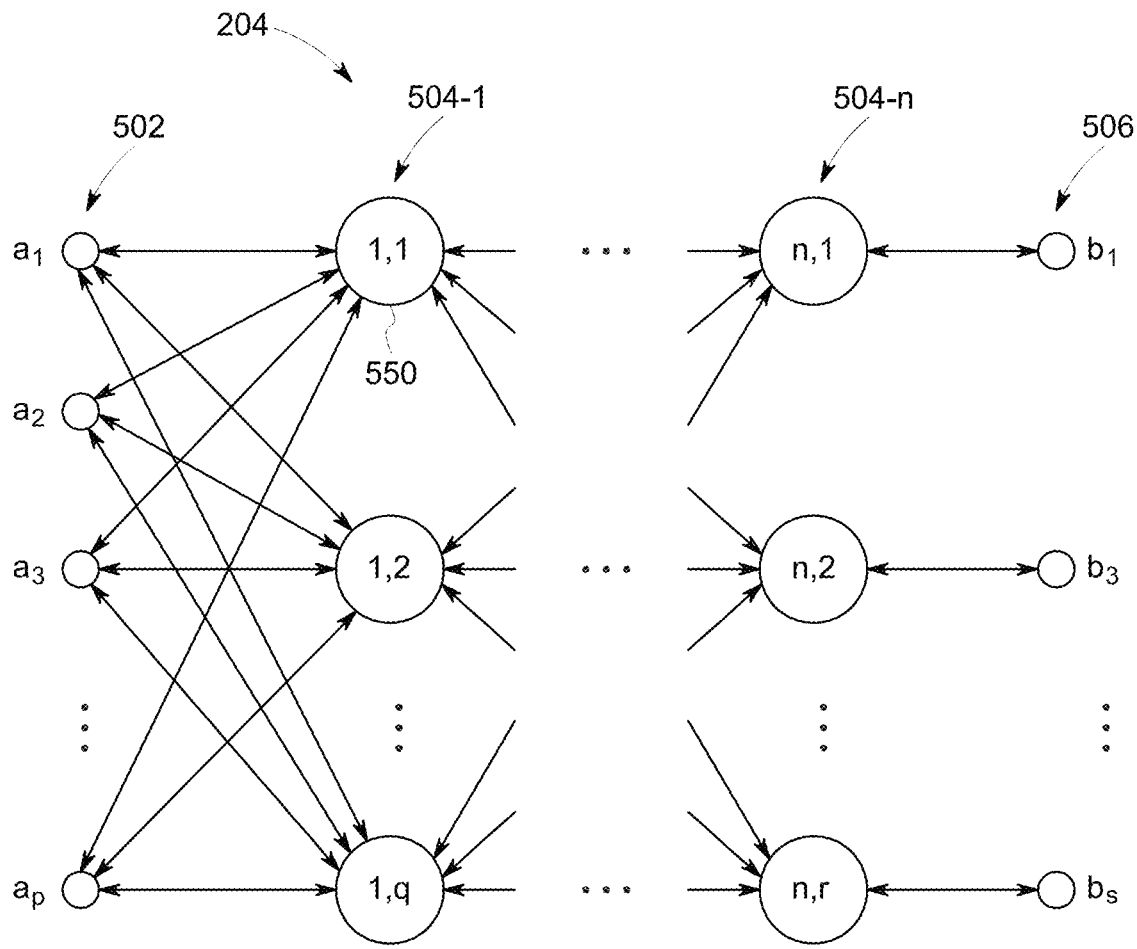
FIG. 8A is a schematic diagram of a neural network model.

FIG. 8A depicts an exemplary artificial neural network model 204. The exemplary neural network model 204 includes layers of neurons 502, 504-1 to 504-n, and 506, including an input layer 502, one or more hidden layers 504-1 through 504-n, and an output layer 506. Each layer may include any number of neurons, i.e., q, r, and n in FIG. 8A may be any positive integers. It should be understood that neural networks of a different structure and configuration from that depicted in FIG. 8A may be used to achieve the methods and systems described herein.

In the exemplary embodiment, the input layer 502 may receive different input data. For example, the input layer 502 includes a first input $a_1$ representing training images, a second input $a_2$ representing patterns identified in the training images, a third input $a_3$ representing edges of the training images, and so on. The input layer 502 may include thousands or more inputs. In some embodiments, the number of elements used by the neural network model 204 changes during the training process, and some neurons are bypassed or ignored if, for example, during execution of the neural network, they are determined to be of less relevance.

In the exemplary embodiment, each neuron in hidden layer(s) 504-1 through 504-n processes one or more inputs from the input layer 502, and/or one or more outputs from neurons in one of the previous hidden layers, to generate a decision or output. The output layer 506 includes one or more outputs each indicating a label, confidence factor, weight describing the inputs, and/or an output image. In some embodiments, however, outputs of the neural network model 204 are obtained from a hidden layer 504-1 through 504-n in addition to, or in place of, output(s) from the output layer(s) 506.

In some embodiments, each layer has a discrete, recognizable function with respect to input data. For example, if n is equal to 3, a first layer analyzes the first dimension of the inputs, a second layer the second dimension, and the final layer the third dimension of the inputs. Dimensions may correspond to aspects considered strongly determinative, then those considered of intermediate importance, and finally those of less relevance.

In other embodiments, the layers are not clearly delineated in terms of the functionality they perform. For example, two or more of hidden layers 504-1 through 504-n may share decisions relating to labeling, with no single layer making an independent decision as to labeling.

Figure 8B:
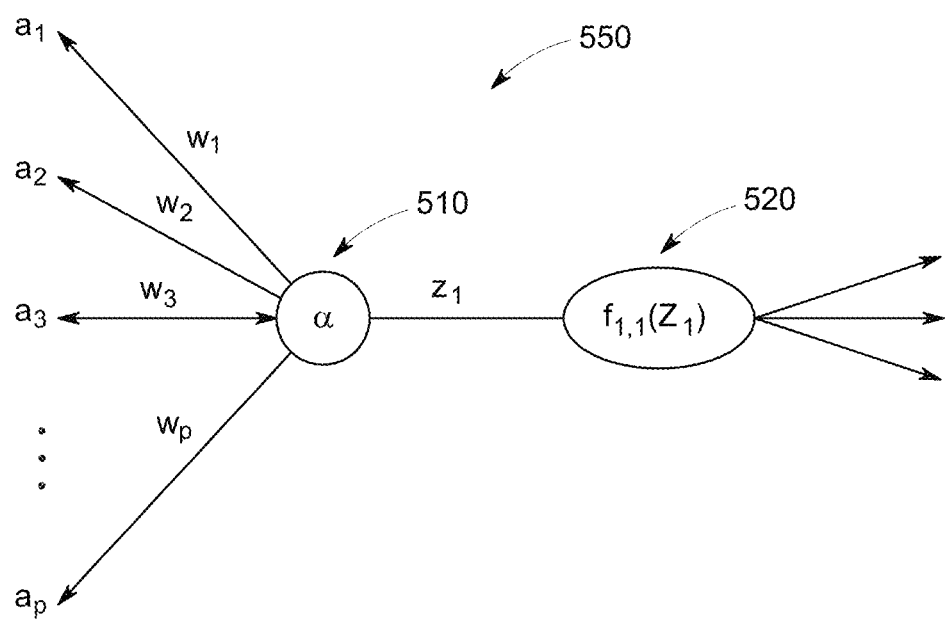
FIG. 8B is a schematic diagram of a neuron in the neural network model shown in FIG. 8A.

FIG. 8B depicts an example neuron 550 that corresponds to the neuron labeled as "1,1" in hidden layer 504-1 of FIG. 8A, according to one embodiment. Each of the inputs to the neuron 550 (e.g., the inputs in the input layer 502 in FIG. 8A) is weighted such that input $a_1$ through $a_p$ corresponds to weights $w_1$ through $w_p$ as determined during the training process of the neural network model 204.

In some embodiments, some inputs lack an explicit weight, or have a weight below a threshold. The weights are applied to a function $\alpha$ (labeled by a reference numeral 510), which may be a summation and may produce a value $z_1$ which is input to a function 520, labeled as $f_{1,1}(z_1)$. The function 520 is any suitable linear or non-linear function. As depicted in FIG. 5B, the function 520 produces multiple outputs, which may be provided to neuron(s) of a subsequent layer, or used as an output of the neural network model 204. For example, the outputs may correspond to index values of a list of labels, or may be calculated values used as inputs to subsequent functions.

It should be appreciated that the structure and function of the neural network model 204 and the neuron 550 depicted are for illustration purposes only, and that other suitable configurations exist. For example, the output of any given neuron may depend not only on values determined by past neurons, but also on future neurons.

The neural network model 204 may include a convolutional neural network (CNN), a deep learning neural network, a reinforced or reinforcement learning module or program, or a combined learning module or program that learns in two or more fields or areas of interest. Supervised and unsupervised machine learning techniques may be used. In supervised machine learning, a processing element may be provided with example inputs and their associated outputs, and may seek to discover a general rule that maps inputs to outputs, so that when subsequent novel inputs are provided the processing element may, based upon the discovered rule, accurately predict the correct output. The neural network model 204 may be trained using unsupervised machine learning programs. In unsupervised machine learning, the processing element may be required to find its own structure in unlabeled example inputs. Machine learning may involve identifying and recognizing patterns in existing data in order to facilitate making predictions for subsequent data. Models may be created based upon example inputs in order to make valid and reliable predictions for novel inputs.

Additionally or alternatively, the machine learning programs may be trained by inputting sample data sets or certain data into the programs, such as images, object statistics, and information. The machine learning programs may use deep learning algorithms that may be primarily focused on pattern recognition, and may be trained after processing multiple examples. The machine learning programs may include Bayesian Program Learning (BPL), voice recognition and synthesis, image or object recognition, optical character recognition, and/or natural language processing—either individually or in combination. The machine learning programs may also include natural language processing, semantic analysis, automatic reasoning, and/or machine learning.

Based upon these analyses, the neural network model 204 may learn how to identify characteristics and patterns that may then be applied to analyzing image data, model data, and/or other data. For example, the model 204 may learn to identify features in a series of data points.

Figure 9:
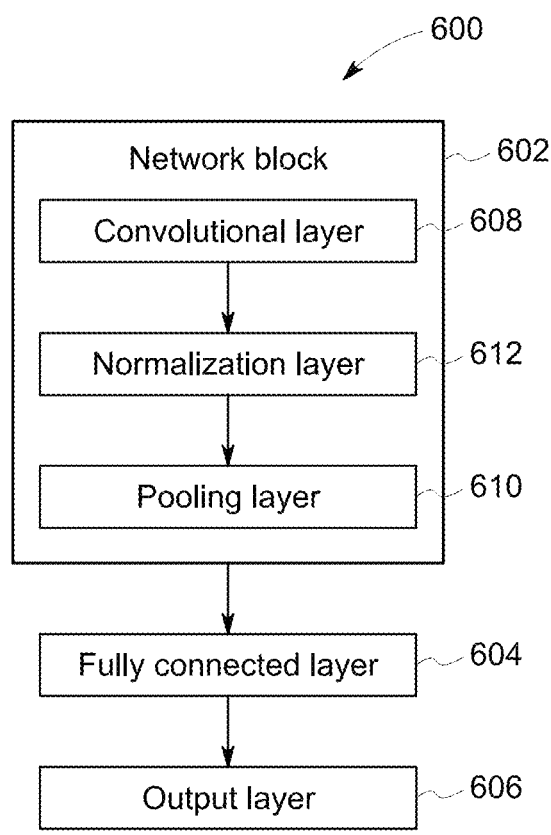
FIG. 9 is a schematic diagram of an exemplary convolutional neural network.

FIG. 9 is a block diagram of an exemplary CNN 600 that may be included in the neural network model 204. The CNN 600 includes a convolutional layer 608. In a convolutional layer, convolution is used in place of general matrix multiplication in a neural network model. In one example, a 1×1 convolution is used to reduce the number of channels in the neural network 600. The neural network 600 includes one or more convolutional layer blocks 602, a fully-connected layer 604 where the neurons in this layer is connected with every neuron in the prior layer, and an output layer 606 that provides outputs.

In the exemplary embodiment, the convolutional layer block 602 includes a convolutional layer 608 and a pooling layer 610. Each convolutional layer 608 is flexible in terms of its depth such as the number of convolutional filters and sizes of convolutional filters. The pooling layer 610 is used to streamline the underlying computation and reduce the dimensions of the data by combining outputs of neuron clusters at the prior layer into a single neuron in the pooling layer 610. The convolutional layer block 602 may further include a normalization layer 612 between the convolutional layer 608 and the pooling layer 610. The normalization layer 612 is used to normalize the distribution within a batch of training images and update the weights in the layer after the normalization. The number of convolutional layer blocks 602 in the neural network 600 may depend on the image quality of training images, and levels of details in extracted features.

In operation, in training, training images and other data such as extracted features of the training images are inputted into one or more convolutional layer blocks 602. Observed masks corresponding to the training images are provided as outputs of the output layer 606. Neural network 600 is adjusted during the training. Once the neural network 600 is trained, an input image is provided to the one or more convolutional layer blocks 602 and the output layer 606 provides outputs that include a mask associated with the input image.

Figure 10:
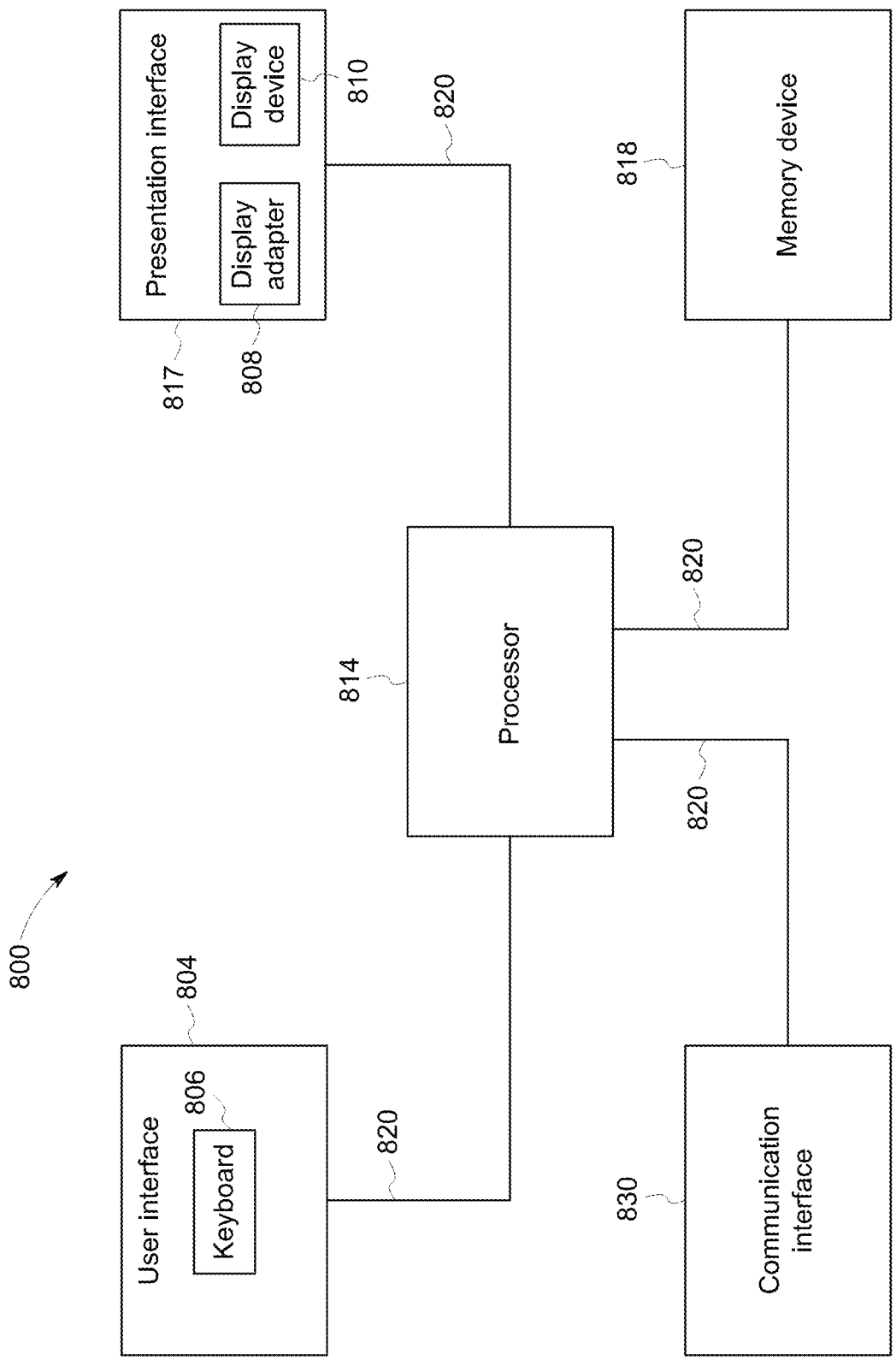
FIG. 10 is a block diagram of an exemplary computing device.

The workstation 12 and the truncation artifact reduction computing device 202, 203 described herein may be any suitable computing device 800 and software implemented therein. FIG. 10 is a block diagram of an exemplary computing device 800. In the exemplary embodiment, the computing device 800 includes a user interface 804 that receives at least one input from a user. The user interface 804 may include a keyboard 806 that enables the user to input pertinent information. The user interface 804 may also include, for example, a pointing device, a mouse, a stylus, a touch sensitive panel (e.g., a touch pad and a touch screen), a gyroscope, an accelerometer, a position detector, and/or an audio input interface (e.g., including a microphone).

Moreover, in the exemplary embodiment, computing device 800 includes a display interface 817 that presents information, such as input events and/or validation results, to the user. The display interface 817 may also include a display adapter 808 that is coupled to at least one display device 810. More specifically, in the exemplary embodiment, the display device 810 may be a visual display device, such as a cathode ray tube (CRT), a liquid crystal display (LCD), a light-emitting diode (LED) display, and/or an "electronic ink" display. Alternatively, the display interface 817 may include an audio output device (e.g., an audio adapter and/or a speaker) and/or a printer.

The computing device 800 also includes a processor 814 and a memory device 818. The processor 814 is coupled to the user interface 804, the display interface 817, and the memory device 818 via a system bus 820. In the exemplary embodiment, the processor 814 communicates with the user, such as by prompting the user via the display interface 817 and/or by receiving user inputs via the user interface 804. The term "processor" refers generally to any programmable system including systems and microcontrollers, reduced instruction set computers (RISC), complex instruction set computers (CISC), application specific integrated circuits (ASIC), programmable logic circuits (PLC), and any other circuit or processor capable of executing the functions described herein. The above examples are exemplary only, and thus are not intended to limit in any way the definition and/or meaning of the term "processor."

In the exemplary embodiment, the memory device 818 includes one or more devices that enable information, such as executable instructions and/or other data, to be stored and retrieved. Moreover, the memory device 818 includes one or more computer readable media, such as, without limitation, dynamic random access memory (DRAM), static random access memory (SRAM), a solid state disk, and/or a hard disk. In the exemplary embodiment, the memory device 818 stores, without limitation, application source code, application object code, configuration data, additional input events, application states, assertion statements, validation results, and/or any other type of data. The computing device 800, in the exemplary embodiment, may also include a communication interface 830 that is coupled to the processor 814 via the system bus 820. Moreover, the communication interface 830 is communicatively coupled to data acquisition devices.

In the exemplary embodiment, the processor 814 may be programmed by encoding an operation using one or more executable instructions and providing the executable instructions in the memory device 818. In the exemplary embodiment, the processor 814 is programmed to select a plurality of measurements that are received from data acquisition devices.

In operation, a computer executes computer-executable instructions embodied in one or more computer-executable components stored on one or more computer-readable media to implement aspects of the invention described and/or illustrated herein. The order of execution or performance of the operations in embodiments of the invention illustrated and described herein is not essential, unless otherwise specified. That is, the operations may be performed in any order, unless otherwise specified, and embodiments of the invention may include additional or fewer operations than those disclosed herein. For example, it is contemplated that executing or performing a particular operation before, contemporaneously with, or after another operation is within the scope of aspects of the invention.

At least one technical effect of the systems and methods described herein includes (a) reduction of truncation artifacts; (b) increase of high spatial frequency information at the same time as reduction of truncation artifacts; (c) one neural network model for reduction of truncation artifacts caused by various partial sampling patterns; and (d) the use of conjugate reflection to increase image quality of images output from the neural network model.

Exemplary embodiments of systems and methods of truncation artifacts reduction are described above in detail. The systems and methods are not limited to the specific embodiments described herein but, rather, components of the systems and/or operations of the methods may be utilized independently and separately from other components and/or operations described herein. Further, the described components and/or operations may also be defined in, or used in combination with, other systems, methods, and/or devices, and are not limited to practice with only the systems described herein.

Although specific features of various embodiments of the invention may be shown in some drawings and not in others, this is for convenience only. In accordance with the principles of the invention, any feature of a drawing may be referenced and/or claimed in combination with any feature of any other drawing.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A computer-implemented method of removing truncation artifacts in magnetic resonance (MR) images, comprising:

receiving a crude image that is based on partial k-space data from a partial k-space asymmetrically truncated in at least one k-space dimension at k-space locations corresponding to high spatial frequencies;

inputting the crude image into a neural network model;

analyzing the crude image using the neural network model, wherein the neural network model was trained with pairs of pristine images and corrupted images, wherein the corrupted images are provided as an input to the neural network and wherein the corrupted images are based on partial k-space data from partial k-spaces truncated in one or more partial sampling patterns at the k-space locations corresponding to the high spatial frequencies, the one or more partial sampling patterns including an asymmetrical truncation in at least one k-space dimension, the pristine images are based on full k-space data corresponding to the partial k-space data of the corrupted images, and target output images of the neural network model are the pristine images;

deriving an improved image of the crude image based on the analysis, wherein the derived improved image includes reduced truncation artifacts and increased high spatial frequency data, compared to the crude image; and outputting the improved image;

wherein the partial k-space data of the corrupted images include k-space data from a partial k-space that is symmetrically truncated in at least one k-space dimension.

2. The method of claim 1, wherein the corrupted images further comprise truncation artifacts represented by residual images, the residual images comprise difference images between the corrupted images and ground truth images of the corrupted images, and the ground truth images are based on the full k-space data corresponding to the partial k-space data of the corrupted images.

3. The method of claim 1, wherein the partial k-space data of the corrupted images include k-space data from a partial k-space that is asymmetrically truncated in more than one k-space dimension.

4. The method of claim 1, wherein the partial k-space data of the corrupted images include a first set of k-space data and a second set of k-space data, wherein the second set of k-space data are conjugate reflections of the first set of k-space data.

5. The method of claim 1, wherein analyzing the crude image further comprises analyzing the crude image and a conjugate reflection image of the crude image, wherein the neural network model further comprises input layers for the conjugate reflection image, and wherein the neural network model takes both the crude image and the conjugate reflection image as inputs.

6. The method of claim 1, wherein the partial k-space data was acquired by a multi-acquisition pulse sequence, and the partial k-space data of each acquisition include partial k-space data from a partial k-space truncated in a complementary partial sampling pattern.

7. The method of claim 1, wherein partial k-space data is acquired by a multi-channel radio-frequency (RF) coil, the method comprising:
for each channel,
receiving a crude image that is based on the partial k-space data acquired by the channel;
analyzing the crude image using the neural network model; and
deriving an improved image of the crude image based on the analysis; and
combining improved images of at least two channels into a combined image.

8. The method of claim 1, wherein the partial k-space data of the corrupted images is symmetrically truncated in the at least one k-space dimension that is different than the at least one k-space dimension in which the partial k-space data of the corrupted images is asymmetrically truncated.

9. A computer-implemented method of removing truncation artifacts in magnetic resonance (MR) images, comprising:
receiving pairs of pristine images and corrupted images, wherein the corrupted images are based on partial k-space data from partial k-spaces truncated in one or more partial sampling patterns at k-space locations corresponding to high spatial frequencies, the one or more partial sampling patterns including an asymmetrical truncation in at least one k-space dimension, the pristine images are based on full k-space data corresponding to the partial k-space data of the corrupted images; and
training a neural network model using the pairs of the pristine images and the corrupted images by:
inputting the corrupted images to the neural network model;
setting the pristine images as target outputs of the neural network model;
analyzing the corrupted images using the neural network model;
comparing outputs of the neural network model with the target outputs; and
adjusting the neural network model based on the comparison,
wherein the trained neural network model is configured to reduce truncation artifacts in the corrupted images and increase high spatial frequency data in the corrupted images;
wherein the partial k-space data of the corrupted images include k-space data from a partial k-space that is symmetrically truncated in at least one k-space dimension.

10. The method of claim 9, wherein the corrupted images further comprise truncation artifacts represented by residual images, the residual images comprise difference images between the corrupted images and ground truth images of the corrupted images, and the ground truth images are based on the full k-space data corresponding to the partial k-space data of the corrupted images.

11. The method of claim 9, wherein the partial k-space data of the corrupted images include k-space data from a partial k-space that is asymmetrically truncated in more than one k-space dimension.

12. The method of claim 9, wherein the partial k-space data of the corrupted images includes a first set of k-space data and a second set of k-space data, wherein the second set of k-space data are conjugate reflections of the first set of k-space data.

13. A truncation artifact reduction system, comprising a truncation artifact reduction computing device, the truncation artifact reduction computing device comprising at least one processor in communication with at least one memory device, and the at least one processor programmed to:
receive a crude image that is based on partial k-space data from a partial k-space asymmetrically truncated in at least one k-space dimension at k-space locations corresponding to high spatial frequencies;
input the crude image into a neural network model;
analyze the crude image using the neural network model, wherein the neural network model was trained with pairs of pristine images and corrupted images, wherein the corrupted images are provided as an input to the neural network and wherein the corrupted images are based on partial k-space data from partial k-spaces truncated in one or more partial sampling patterns at the k-space locations corresponding to the high spatial frequencies, the one or more partial sampling patterns including an asymmetrical truncation in at least one k-space dimension, the pristine images are based on full k-space data corresponding to the partial k-space data of the corrupted images, and target output images of the neural network model are the pristine images;
derive an improved image of the crude image based on the analysis, wherein the derived improved image includes reduced truncation artifacts and increased high spatial frequency data, compared to the crude image; and
output the improved image;
wherein the partial k-space data of the corrupted images include k-space data from a partial k-space that is symmetrically truncated in at least one k-space dimension.

14. The system of claim 13, wherein the corrupted images further comprise truncation artifacts represented by residual images, the residual images comprise difference images between the corrupted images and ground truth images of the corrupted images, and the ground truth images are based on the full k-space data corresponding to the partial k-space data of the corrupted images.

15. The system of claim 13, wherein the partial k-space data of the corrupted images include k-space data from a partial k-space that is asymmetrically truncated in more than one k-space dimension.

16. The system of claim 13, wherein the partial k-space data of the corrupted images includes a first set of k-space data and a second set of k-space data, wherein the second set of k-space data are conjugate reflections of the first set of k-space data.

17. The system of claim 13, wherein the at least one processor is further programmed to analyze the crude image and a conjugate reflection image of the crude image, wherein the neural network model takes both the crude image and the conjugate reflection image as inputs.

18. The system of claim 13, wherein the partial k-space data was acquired by a multi-acquisition pulse sequence, and the partial k-space data of each acquisition include partial k-space data from a partial k-space truncated in a complementary partial sampling pattern.

* * * * *